(12) United States Patent
Msika

(10) Patent No.: US 9,125,879 B2
(45) Date of Patent: Sep. 8, 2015

(54) COMPOSITION CONTAINING A QUINOA EXTRACT FOR DERMATOLOGICAL USE

(75) Inventor: Philippe Msika, Versailles (FR)

(73) Assignee: LABORATOIRES EXPANSCIENCE, Courbevoie (FR)

( * ) Notice: Subject to any disclaimer, the term of this patent is extended or adjusted under 35 U.S.C. 154(b) by 1642 days.

(21) Appl. No.: 12/521,371

(22) PCT Filed: Dec. 28, 2007

(86) PCT No.: PCT/EP2007/064623
§ 371 (c)(1),
(2), (4) Date: Oct. 27, 2009

(87) PCT Pub. No.: WO2008/080974
PCT Pub. Date: Jul. 10, 2008

(65) Prior Publication Data
US 2010/0136144 A1    Jun. 3, 2010

(30) Foreign Application Priority Data
Dec. 28, 2006   (FR) ..................................... 06 56001

(51) Int. Cl.
| | |
|---|---|
| *A61K 36/21* | (2006.01) |
| *A61Q 19/08* | (2006.01) |
| *A23D 9/007* | (2006.01) |
| *A23J 3/34* | (2006.01) |
| *A23L 1/10* | (2006.01) |
| *A23L 1/30* | (2006.01) |
| *A23L 1/305* | (2006.01) |
| *A61K 8/92* | (2006.01) |

(52) U.S. Cl.
CPC ................ *A61K 36/21* (2013.01); *A23D 9/007* (2013.01); *A23J 3/346* (2013.01); *A23L 1/1041* (2013.01); *A23L 1/3008* (2013.01); *A23L 1/3053* (2013.01); *A61K 8/922* (2013.01); *A61Q 19/08* (2013.01); *A23V 2002/00* (2013.01)

(58) Field of Classification Search
CPC ...... A61K 36/21; A23L 1/3053; A61Q 19/08; A23V 2200/318; A23V 2200/304
See application file for complete search history.

(56) References Cited

U.S. PATENT DOCUMENTS

| | | |
|---|---|---|
| 5,334,290 A | 8/1994 | Nuns et al. |
| 6,146,616 A | 11/2000 | Msika et al. |
| 6,355,249 B2 | 3/2002 | Muir et al. |
| 6,582,688 B1 | 6/2003 | Broutin et al. |
| 7,563,473 B2 | 7/2009 | Scanlin et al. |
| 2007/0122492 A1 | 5/2007 | Behr et al. |
| 2008/0113921 A1 | 5/2008 | Piccirilli et al. |

FOREIGN PATENT DOCUMENTS

| | | |
|---|---|---|
| EP | 0 493 144 | 7/1992 |
| FR | 2760746 A1 * | 9/1998 |
| WO | WO 98/47479 | 10/1998 |
| WO | WO 99/53933 | 10/1999 |
| WO | WO 01/21150 | 3/2001 |
| WO | WO 01/21605 | 3/2001 |
| WO | WO2005/004831 | 1/2005 |
| WO | WO 2005/058249 | 6/2005 |
| WO | WO 2005/115421 | 12/2005 |
| WO | WO 2006/053415 | 5/2006 |

OTHER PUBLICATIONS

International Search Report, issued on Jun. 4, 2008, in application No. PCT/EP2007/064623.
French Search Report, issued on Oct. 10, 2007, in application No. FR 0656001.
Aluko et al., "Functional and Bioactive Properties of Quinoa Seed Protein Hydrolysates," *Journal of Food Science*, vol. 68, No. 4, pp. 1254-1258 (2003).
Przybylski et al., "Characterization of quinoa (*Chenopodium quinoa*) lipids," *Food Chemistry*, vol. 51, pp. 187-192 (1994).
Koziol, "Quinoa: A Potential New Oil Crop," *New Crops*, J. Janick and J.E. Simon (eds.), Wiley, New York, pp. 328-336 (1993).

\* cited by examiner

*Primary Examiner* — Michele Flood
(74) *Attorney, Agent, or Firm* — Foley & Lardner LLP

(57) ABSTRACT

The present invention relates to a composition containing a *quinoa* grain extract, said extract being a peptidic and osidic extract or a lipidic extract of *quinoa* grain, said lipid *quinoa* extract being itself chosen from a group comprising an oil concentrated into its non saponificable fraction, a non saponificable, or a refined oil. The invention also relates to methods for preparing these different extracts and to dermatological or neutraceutic applications of these extracts.

5 Claims, 3 Drawing Sheets

COMPOSITION CONTAINING A QUINOA EXTRACT FOR DERMATOLOGICAL USE

Figure 1:
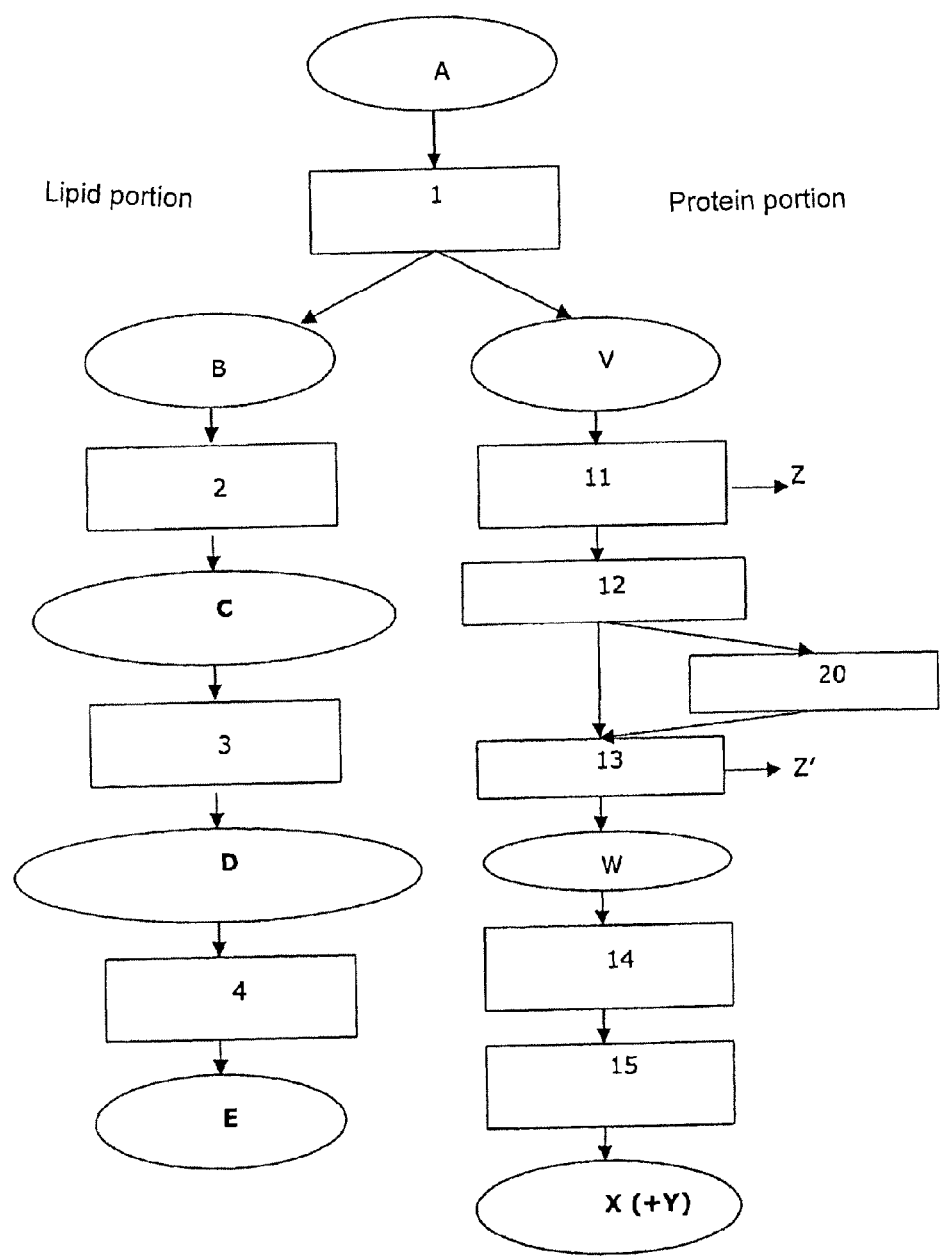

The invention relates to a cosmetic, dermatological or neutraceutical composition comprising a suitable excipient and an extract of *quinoa* grains.

*Quinoa* grain is classified among the pseudo-cereals because of taxonomic considerations and of a chemical composition which links it to grasses. Although its richness in proteins and in several minerals was recognized as soon as the beginning of the 20$^{th}$ century, its consumption remained confined to the Andes Cordillera for more than 6,000 years. In the Quechua language originating from the Incas, the word *quinoa* means "chisiya mama" or "mother seed" in Spanish. In the 18$^{th}$ and 19$^{th}$ centuries, traveling botanists who cross the Andean regions spoke very highly of it. Attempts for cultivating it which they made in Europe were not very conclusive. A German horticulturist asserted in 1917 that tests had been successful but the latter fell into oblivion. Because of proved nutritional benefit, of many investigations conducted for the past thirty years and of the curiosity which it raises, *quinoa* grain is increasingly attractive. The botanical name of *quinoa* is *Chenopodium quinoa* Willd. Subsp. *quinoa*. Its usual and vernacular names are:

in quechua: quinua, kiuna; (there exist many other names in South America);
  in Spanish: *quinoa*, quinua, arroz del Peru,
  in French: *quinoa*, petit riz, riz du Pérou;
  in English: *quinoa*, quinua.

*Chenopodium quinoa* is a yearly herbaceous plant with a height measuring 0.5 to 2.1 meters depending on the environmental conditions and on the genotype (cultivated plants from 1 to 1.5 meter). The pivot root is densely branched, which facilitates its resistance to frost. The aerial portion either appears branched or not depending on the varieties. Its alternate leaves are quite polymorphous (lanceolate, deltoid or triangular). They are green when the plant is still young and assume a yellow, red or purple color upon maturity. Inflorescence is of the panicle type. The apetalous flowers are small and sessile.

Indehiscent fruit is an achene. It contains small almost spherical grains measuring from 1 to 2.0-2.6 mm in diameter and the aspect of which recalls that of millet. Their color is white, yellow red, purple, brown or black. The pericarp accounts for about 8% of the grain, the embryo 60-69% and the perisperm about 23%.

Among the *Chenopodium* genus, two wild species, *C. hircinum* and *C. berlandieri*, are close to *Chenopodium quinoa* (same number of chromosomes (2n=36) and interspecific hybridizations). Hybridization cases have been also observed between *quinoa* and white chenopod (*Chenopodium album* L.).

Cultivated quinoas have large variabilities in colors (plants, inflorescences, seeds), in protein and saponin contents in the grains, and beta-cyanine and calcium oxalate contents in the leaves.

The Andean region and more particularly the banks of the lake Titicaca, are found to have a large genetic diversity of population. The main known varieties in this region are the following:

in Peru: Kancolla, Cheweca, Witulla, Tahuaco, Camacani, Yocaré, Wilacayuni, Blanca de Juli, Amarilla de Marangani, Pacus, Rosada, Blanca de Junin, Hualhuas, Huancayo, Mantaro, Huacariz, Huacataz, Acostambo, Blanca Ayacuchana and Nariño.
  in Bolivia: Sajama, Real Blanca, Chucapaca, Kamiri, Huaranga, Pasancalla, Pandela, Tupiza, Jachapucu, Wila Coymini, Kellu, Uthusaya, Chullpi, Kaslali and Chillpi;
  in Ecuador: Inbaya, Chaucha, INIAP-Cochasqui, Tanlahua, Piartal, Porotoc, Amarga del Chimborazo, Amarga de Imbabura and Morada;
  in Columbia: Dulce de Quitopampa;
  in Argentina: Blanca de Jujuy;
  in Chile: Baer, Lito, Faro and Picchaman.

In 1968, a Bolivian botanist described 17 races according to their morphological characters. Other botanists have proposed four main ecotypes defined according to their geographical localization: the "Valley" type, typical of an altitude of 2,000-4,000 m; the "Altiplano" type, typical of highlands located above 4,000 m; the "Salted" type located around 4,000 m but adapted to the strong pHs of the soils of the Atacama region; and the "Sea level" types encountered in the inner valleys of Bolivia. Wild *quinoa* originates from the high plateaus of the Andes Cordillera. It is encountered in Peru, Bolivia, and in the extreme North of Chile at altitudes which may exceed 3,900 m.

Dry *quinoa* grains consist of water (about 10%, a reported value of 12.6% in the literature), of mineral materials (values from 2.46 to 3.4% reported in the literature), of carbohydrates (values of 58.5% and 61.2% reported in the literature for raw grains, and of 62.8% for polished grains), of proteins (values from 12.2 to 13.8% reported in the literature, 14.8 and 15.7% for sweet and bitter quinoas respectively), of lipids (values varying from about 4.5 to about 10% reported in the literature), saponosides and polyphenols. The indicated percentages are expressed by weight based on the total weight of the dry grain.

As carbohydrates, the dry grain of *quinoa* comprises alimentary fibers (a value of 6.6% reported in the literature), raw fibers (value of 2.2% reported in the literature) including water-soluble fibers (1.26 g/100 g according to the literature) and fibers insoluble in water (5.38 g/100 g according to the literature). Glucose (4.5% according to the literature), fructose (2.4% according to the literature) and saccharose (2.4% according to the literature) are substantial. The indicated percentages are expressed by weight based on the total content by weight of carbohydrates in the dry grain.

As lipids, the dry *quinoa* grain comprises fatty acids, phosphatides (mainly lysophosphatidylethanolamine) tocopherols (mainly α-tocopherol and γ-tocopherol), hydrocarbons (squalene) and sterols.

The majority fatty acids are linoleic acid and oleic acid. The dry grain also contains significant amounts of palmitic acid and α-linolenic acid. It may also contain myristic acid, 5-hexadecenoic acid, stearic acid, arachidic acid, eicasenoic acid, behenic acid, 9-docosenoic acid, tetracosenoic acid or other acids. The raw grains and the polished and washed grains have very close fatty acid proportions.

In the literature, high levels of free fatty acids are reported: 18.9% in the entire grain; an iodine number of 129; a saponification number of 190, a 5.2% content of unsaponifiable material.

According to the literature, the majority sterols are Δ7-stigmasterol. The other sterols which may be present are Δ5,24 (28)-avenasterol, β-sitosterol, Δ7-campesterol, stigmasterol, cholesterol, campesterol, fucostanol, 24-ethylene-Δ7-cholesten-3β-ol.

Saponosides present in the *quinoa* grain have been extensively studied for 25 years by researchers from different continents. These are triterpenic saponosides. These constituents are essentially located at the pericarp of the grain.

The applications of *quinoa* and of its extracts except for saponine, were hitherto confined to the food industry domain. As an example, international application WO2005/058249 may be mentioned, which describes a protein concentrate used in the food industry.

International application WO2006/053415 discloses dermatological uses of many extracts of plants including *quinoa*. *quinoa* extracts are obtained by aqueous or ethanol extraction on stressed and non-stressed plants. The thereby obtained aqueous extract contains a few water-soluble proteins, tannins, free sugars and oligosaccharides, heterosides (saponins+flavonics). The ethanol extract as for it contains saponins, polyphenols, triterpenic lipids, and a few lipids. However, the tests conducted on interleukin IL-8 show that the tested extract induces the synthesis of this interleukin IL-8 and the conclusion has therefore to be drawn that this extract is pro-inflammatory. Thus, in fact, it is not recommended for dermatological use. No serious dermatological use of *quinoa* and of its extracts has therefore been contemplated hitherto.

Now, the inventors have surprisingly discovered, that certain *quinoa* extracts are not inflammatory and have interesting cosmetic, dermatological or nutraceutical properties.

The object of the invention is therefore a cosmetic, dermatological or nutraceutical composition comprising an extract of *quinoa* grains and, if necessary, a suitable excipient, characterized in that said extract is a peptide extract or a lipid extract of *quinoa* grains. The nutraceutical composition may not comprise any excipient.

FIG. 1 identifies the different steps for obtaining various lipid and peptide extracts. Starting with *quinoa* grains (A), the method comprises a first step (1) for extraction by pressure, by solvent, under supercritical pressure. From this extract, either the lipid portion (raw oil B) or the peptide portion (cake V) are beneficiated. The raw oil is subject to refining (2) in order to lead to a refined oil (C). This refined oil (C) is subject to molecular distillation (3) in order to lead to a concentrated oil in its unsaponifiable fraction (or concentrate D). This concentrated oil (D) is then subject to saponification and extraction (4) in order to lead to the unsaponifiables (E). As regards the protein portion, the cake (V) is washed with water and/or ethanol (11) in order to suppress the saponins, soluble sugars, heterosides and polyphenols (Z). The washed cake is then subject to a step for solubilizing proteins at an alkaline pH (12). As an alternative, the method may comprise an additional enzymatic treatment step with α-amylase/cellulase (20). The method then comprises a centrifugation step and then an ultrafiltration step (13), which allows the insolubles (Z') to be removed and leads to concentrated proteins (W). These concentrated proteins (W) are then subject to an enzymatic treatment step with proteases (14) and then to heat treatment, ultrafiltration and nanofiltration (15), which leads to the peptides (X) (+sugars Y).

According to a first alternative of the invention, the *quinoa* extract is a lipid extract of *quinoa* grains. The oils may be extracted by several methods:
- physical extraction such as hot pressing on a mechanical press, pressing on a double screw extruder;
- chemical extraction by means of organic solvents (aliphatic alkanes, alcohols, chlorinated solvents, fluorinated solvents);
- extraction in a supercritical medium, with carbon dioxide alone and/or with co-solvents.

Before extracting the oil, the saponins contained in majority on the outer wall of the grains, are advantageously removed beforehand by abrasive husking or by washing with water. Moreover, the grains may have been treated hydrothermally beforehand.

For extracting raw *quinoa* oil, the use of a chemical solvent of the aliphatic alkane type, such as n-hexane, will be preferred. According to a particular mode of extraction, the husked and washed, possibly hydrothermally pre-treated, grains are flattened in order to obtain flakes, before being introduced into a continuous belt extractor, and the lipids are extracted by percolation of n-hexane. The collected miscella is evaporated in vacuo in order to recover the desolvented oil.

The specifications of the raw *quinoa* oil are given in the following Table 1:

TABLE 1 specifications of raw quinoa oil
Fat cut (% by weight based on the total weight of the oil)

| | |
|---|---|
| C14 (myristic acid) | ≤1.0 |
| C16 (palmitic acid) | 5.0-12.0 |
| C16' (5-hexadecenoic acid) | ≤1.0 |
| C18 (stearic acid) | ≤2.0 |
| C18' (oleic acid) | 20.0-35.0 |
| C18" (linoleic acid) | 40.0-60.0 |
| C18'" (α-linolenic acid) | 2.0-13.0 |
| C20 (arachidic acid) | ≤1.0 |
| C20' (eicasenoic acid) | ≤3.0 |
| C22 (behenic acid) | ≤1.0 |
| C22' (9-docosenoic acid) | ≤3.0 |
| C24 (tetracosenoic acid) | ≤1.0 |
| Tocopherol content (mg/100 g) | 4-300 |
| Sterol content (g/100) | 1.0-3.0 |
| Squalene content (g/100) | 1.0-5.0 |
| Unsaponifiable content (g/100) | 3.0-8.0 |

This oil is alimentary. As such, it may be consumed by humans. It therefore observes the CODEX standards. It contains no or very little free fatty acids. According to the standards in force, the maximum values of the acid number are 0.4 mg KOH/g of oil, for oil obtained by cold pressing and virgin oils. It does not contain any oxidation byproducts or residual products of the plant protective residue and HAP (polycyclic aromatic hydrocarbon) type.

Raw *quinoa* oil may be refined according to methods known to one skilled in the art such as physical refining (degumming with water, deacidification by deodorization at high temperature) and chemical refining (mucilage removal with water or an acid treatment in order to remove phospholipids, neutralization of free fatty acids by means of a basic solution, discoloration, frigelization, and deodorization). Chemical refining will be preferred because it allows removal of the saponins carried away during extraction, as well as of the strong proportion of phospholipids and of free fatty acids.

The specifications of refined *quinoa* oil according to the invention are given in the following Table 2:

TABLE 2 specifications of refined quinoa oil
Fat cut (% by weight based on the total weight of the oil)

| | |
|---|---|
| C14 | ≤1.0 |
| C16 | 5.0-12.0 |
| C16' | ≤1.0 |
| C18 | ≤2.0 |
| C18' | 20.0-35.0 |
| C18" | 40.0-60.0 |
| C18'" | 2.0-13.0 |
| C20 | ≤1.0 |
| C20' | ≤3.0 |
| C22 | ≤1.0 |
| C22' | ≤3.0 |
| C24 | ≤1.0 |
| Tocopherol content (mg/100 g) | 4-200 |
| Sterol content (g/100) | 0.5-3.0 |

TABLE 2-continued specifications of refined quinoa oil
Fat cut (% by weight based on the total weight of the oil)

| | |
|---|---|
| Squalene content (g/100) | 0.5-3.0 |
| Unsaponifiable content (g/100) | 2.0-6.0 |

This oil is alimentary. As such, it may be consumed by human. It therefore observes the CODEX standards. It contains no or very little free fatty acids. According to the standards in force, the maximum values of acid number are 0.6 mg/KOH/g of oil, for refined oils. It does not contain any oxidation byproducts or residual products of the plant protective residue and HAP (polycyclic aromatic hydrocarbon) type. It also has triglycerides, for which the fatty acid distribution is identical with that of the initial oil, so that it may benefit from the designation of natural vegetable oil.

The object of the invention is also a method for preparing a refined *quinoa* oil having specifications as defined in Table 2, comprising a step for chemical refining of the raw *quinoa* oil. According to an advantageous alternative, the method comprises the steps descried earlier.

The refined *quinoa* oil obtained earlier may be concentrated into its unsaponifiable fraction by a molecular distillation method.

The unsaponifiable fraction is the fraction of a fat which after prolonged action of an alkaline base remains insoluble in water and may be extracted with an organic solvent. Five large groups of substances are present in most unsaponifiables of vegetable oils: saturated or unsaturated hydrocarbons, aliphatic or terpenic alcohols, sterols, tocopherols, carotenoid and xanthophyl pigments.

This molecular distillation step is preferably conducted by using a device selected from molecular distillers of the centrifuge type and molecular devices of the scraped film type.

Molecular distillers of the centrifuge type are known to one skilled in the art. For example, patent application EP 493 144 describes a molecular distiller of this type. Generally, the product to be distilled is spread out as a thin layer on the heated surface (hot surface) of a conical rotor rotating at high speed. The distillation enclosure is placed in vacuo. Under these conditions, there is evaporation and no boiling, from the hot surface of the constituents of the oil such as the unsaponifiables, the advantage being that the oil and its constituents, notably the unsaponifiables (these products are notoriously fragile), are not degraded during evaporation.

The molecular distillers of the scraped film type are also known to one skilled in the art. Generally, they comprise a distillation chamber provided with a rotating scraper, with which the products to be distilled may be spread out continuously over the evaporation surface (hot surface). The product vapors are condensed by means of a refrigerated finger, placed at the centre of the distillation chamber. The feeder and vacuum peripheral systems are very close to those of a centrifugal distiller (feeder pumps, vacuum vane pumps and oil diffusion pumps, etc.). The recovery of the residues and of the distillates in glass flasks is accomplished by gravitational flow.

At the end of the fractionation step, the distilled fraction rich in unsaponifiables advantageously accounts for 5-15% by weight of the initial oil, and the distilled fraction rich in triglycerides advantageously accounts for 85-95% by weight of the initial oil. It has additionally been checked that this method did not cause any chemical modification or alteration of the compounds of the unsaponifiable, and that the strongly unsaturated fractions were preserved. Therefore, the fatty acid distribution of concentrated *quinoa* oil is identical with that of *quinoa* oil before concentration.

According to an advantageous alternative of the invention, concentrated *quinoa* oil in its unsaponifiable fraction has the specifications given in the following Table 3:

TABLE 3 specifications of a refined oil concentrated in its unsaponifiable fraction
Fat cut (% by weight based on the total weight of the oil)

| | |
|---|---|
| C14 | ≤1.0 |
| C16 | 5.0-15.0 |
| C16' | ≤1.0 |
| C18 | ≤2.0 |
| C18' | 20.0-35.0 |
| C18" | 40.0-60.0 |
| C18'" | 2.0-13.0 |
| C20 | ≤1.0 |
| C20' | ≤3.0 |
| C22 | ≤1.0 |
| C22' | ≤3.0 |
| C24 | ≤1.0 |
| Tocopherol content (mg/100 g) | 40-5,000 |
| Sterol content (g/100) | 3.0-20.0 |
| Squalene content (g/100) | 2.0-40.0 |
| Unsaponifiable content (g/100) | 5.0-50.0 |

This refined oil enriched in its unsaponifiable fraction per se is a novel food, also object of the present invention. As such, it may be consumed by humans. It therefore observes the CODEX standards. It contains no or very little free fatty acids. Within the scope of an approval procedure for a novel food product before competent authorities, maximum acid number values will be defined.

Further, it does not contain any oxidation byproducts or residual products of the plant-protective residue and HAP (polycyclic aromatic hydrocarbon) type. It also has triglycerides, for which the fatty acid distribution is identical with that of the initial oil, so that it may benefit from the designation of natural vegetable oil.

As this refined oil is enriched in its unsaponifiable fraction, it may provide the organism, for a same provision of triglycerides as refined oil, larger amounts of nutritious elements, such as phytosterols and vitamins, without additional caloric intake.

The object of the invention is also a method for preparing a *quinoa* oil concentrated in its unsaponifiable fraction, comprising a step for molecular distillation of refined *quinoa* oil. In particular, the molecular distillation step is carried out by using a device selected from molecular distillers of the centrifugal type and molecular devices of the scraped film type. The method advantageously comprises the steps described earlier.

Unsaponifiables of *quinoa* oil may be obtained by methods known to one skilled in the art. For example, they may be obtained by carrying out saponification on *quinoa* oil concentrated in its unsaponifiable fraction, and then by extracting this unsaponifiable with a suitable solvent. This extract is then washed until complete removal of the soaps and then the solvent is evaporated. Finally the unsaponifiable is advantageously subject to deodorization with steam and then stripping with nitrogen in order to remove traces of solvent.

*Quinoa* oil unsaponifiables advantageously have the specifications given in the following Table 4:

TABLE 4

| specifications of a quinoa oil unsaponifiable | |
| --- | --- |
| Tocopherol content (g/100 g) | 1.5-3.5 |
| Sterol content (g/100 g) | 20.0-50.0 |
| Squalene content (g/100 g) | 20.0-50.0 |

The invention also relates to a method for preparing a *quinoa* unsaponifiable comprising a step for saponification of a *quinoa* oil concentrated in its unsaponifiable fraction, and then extraction of this unsaponifiable with a suitable solvent. The method advantageously comprises the steps described earlier.

Within the scope of the invention, the lipid extract of *quinoa* grains is itself selected from the group formed by an oil concentrated in its unsaponifiable fraction, an unsaponifiable or a refined oil having the specifications given earlier (Table 2).

According to a second alternative of the invention, the *quinoa* extract is a peptide and oside extract of *quinoa* grains.

The peptide and oside extract is advantageously obtained by a method comprising the following successive steps:
a) starting with *quinoa* grains, extraction of a raw oil and of a cake and recovery of said cake;
b) washing said cake with water or with a water/alcohol mixture in order to only retain the protein portion, and then
c) solubilizing the proteins;
d) concentrating the proteins and then hydrolyzing said proteins into peptides;
e) purifying and recovering the peptide extract.

The peptide and oside extract according to the invention advantageously has the following specifications:

TABLE 5

| specifications of a peptide extract of *quinoa* % by weight based on the total weight of the peptide extract | |
| --- | --- |
| Peptide content (%) | 25-90 |
| Total sugar content (%) | 10-50 |

The object of the invention is also a method for preparing a peptide and oside extract of *quinoa*, comprising the following successive steps:
a) starting with *quinoa* grains, extraction of a raw oil and of a cake and recovery of said cake;
b) washing said cake with water or with a water/alcohol mixture in order to only retain the protein portion, and then
c) solubilizing the proteins;
d) concentrating the proteins and then hydrolyzing said proteins into peptides;
e) purifying and recovering the peptide extract.

Moreover, prior to concentrating the proteins (step d), the fibers are advantageously removed.

A preferred embodiment for obtaining the peptide and oside extract is described hereafter.

The cake of *quinoa* grains obtained after removal of the solvent, during extraction of lipids, is dispersed in water or in a water/ethanol mixture in order to extract and remove the saponosides, heterosides and polyphenols. This mixture is spin-dried or centrifuged in order to recover the pellet and the juice is discarded. The pellet is dispersed and mixed in water, at an alkaline pH comprised between 8 and 13, in order to solubilize the proteins. It is possible to either remove the fibers by fresh centrifugation or by carrying out hydrolysis of the starch and of the fibers (cellulose, hemicellulose, . . . ) with a mixture of α-amylases and cellulases.

The soluble proteins are then either concentrated by precipitation in an acid medium at the isoelectric point, or by ultrafiltration. The concentrated proteins are then hydrolyzed by enzymes, advantageously alkaline proteases. With a heat treatment, it is possible to denaturate the enzymes at the end of the reaction.

The reaction medium is subject to ultrafiltration on a membrane having a cut-off threshold of 10 kDa in order to remove the residual proteins (retentate). The permeate is then concentrated to the desired dry material level and desalted by nanofiltration with a membrane having a cut-off threshold of 200 Da. Finally, the product is conditioned after having been filtered sterilely (0.2 μm).

The composition may further comprise at least one compound selected from the group formed by
actives conventionally used in dermatology such as emollients, moisturizing active agents, activators for keratin synthesis, kerato-regulators, keratolytic agents, skin barrier restructuring agents (activators of skin lipid synthesis, PPAR (Peroxysome Proliferator Activated Receptor) agonists, RxR or LXR agonists, SERMs, agonists of vitamin D or corticoid receptors, keratinocytes differentiation activators (retinoids, Calcidone®, calcium), sebo-regulators (inhibitors of 5-alpha reductase, notably the 5-alpha active Avocuta® marketed by Laboratoires Expanscience), preservatives, anti-irritation agents, soothing agents, solar filters and screens, anti-oxidants,
active ingredients having a complementary therapeutic action, such as antibiotics, pre- and pro-biotics, antibacterial agents, antifungic compounds, anti-viral agents, immunomodulators (tacrolimus or pimecrolimus), oxazolines, growth factors, healing agents or eutrophic molecules, drugs, anti-inflammatory agents, pigmentary or hypopigmentary agents, lipolytic agents or inhibitors of lipogenesis, pigmentary or ultrafine mineral or organic solar filters and screens, conventional or functional foods: hyper- or hypoglycemics, anti-fat or anti-cellulitis nutrients, anti-cholesterol, antioxidant, energizing, invigorating nutrients, having an impact on secondary signs of menopause,
natural plant extracts (vegetable portions extractable in an aqueous or oily phase: polyphenols, flavonoids, other peptides and sugars, . . . ), compounds containing unsaponifiables of vegetable oils, sterol unsaponifiables or products which may contain them (unsaponifiables of vegetable oils, notably unsaponifiables of soya bean oil, unsaponifiables of vegetable butters, or butyrous materials and their mixtures, unsaponifiables of natural waxes, unsaponifiables of oil extracts, unsaponifiables of industrial oily co-products, unsaponifiables of fat extracts of animal origin, unsaponifiables of marine oils, unsaponifiables of lactic fat extracts, unsaponifiables of lipids extracted from unicellular organisms, unsaponifiables of lipids extracted from algae and marine organisms, etc.), sterols, stanols, phytosterols, phytostanols, tocopherols, concentrates of sunflower, rapeseed and/or palm oils, oligo-elements, vitamins, omega 3, 6 or 9 fatty acids, hypoglycaemic or hyperglycaemic or sweetening plants.

The activators of keratin synthesis which may be used in association, are advantageously retinoids, lupin peptides marketed by Silab, key proteins from the stratum corneum or granulosum (keratins) and corneodesmosomes.

The soothing agents which may be used in association, are advantageously alpha bisabolol, licorice derivatives, ibuprofene, enoxolone. The keratoregulators which may be used in association, are advantageously alpha hydroxyl acids and their derivatives. A keratolytic agent which may be used in association, is notably salicylic acid and its derivatives.

The growth factors which may be used in association, are advantageously becaplermine and TGF-beta (Transforming Growth Factor beta), EGF, NGF, VEGF.

The antioxidants which may be used in association, are advantageously selected from the group formed by oligoelements (copper, zinc, selenium), lipoic acid, alone or associated with vitamin B12, vitamins C, vitamins E, flavonoids (green tea, . . . ), beta-carotene, lycopene, or lutein, antiglycation substances such as carnosine, n-acetyl-cysteine, soya bean isoflavones, soya bean proteins, as well as antioxidant or radical enzymes, SOD (Super Oxide Dismutase) catalase, glutathion peroxidase, thioredoxin reductase and their agonists.

The skin barrier restructuring agents allows stimulation of the synthesis of key lipids of the epidermis, and which may be used in association, are advantageously sunflower concentrates, more advantageously linoleic sunflower concentrates, such as the active product marketed by Laboratoires Expanscience, Soline® (cf. international application WO 01/21150), unsaponifiables of vegetable oil, such as Avocadofurane® (cf. international application WO 01/21150), PPAR agonists (rosiglitazone, pioglitazone), RxR, LXR.

The antifungic compounds which may be used in association, are advantageously econazole and ketoconazole.

Antiseptic preservatives which may be used in association, are for example triclosan, chlorhexidine, quaternary ammoniums.

The antibiotics which may be used in association, are advantageously fucidic acid, penicillin, tetracyclins, pristinamycin, erythromycin, clindamycin, mupirocin, minocyclin, doxycyclin. The antiviral agents which may be used in association, are advantageously acyclovir and valacyclovir. The anti-irritation agents which may be used in association, are advantageously glycine, sugars and/or lupin peptides, Cyclocéramide® (oxazolin derivative).

The healing agents which may be used in association, are advantageously vitamin A, panthenol, Avocadofurane®, zinc oxide, magnesium, silicon, madecassic or asiatic acid, dextran sulfate, glucosamine, chondroitin sulfate and globally GAGs, peptides of soya bean either fermented or not, oligoelements.

The drugs which may be used in association, are advantageously the drugs suitable for administration via a topical or oral route, for preventing and/or treating atopia (corticoids, topical immunomodulators, inhibitors of calcineurin, emollients), acne (antibiotics, benzoyl peroxide, retinoids, azelaic acid, vitamin PP, vitamin B3, zinc, cyclins), eczema (immunomodulators, emollients, salmon oil, borage oil, pre-biotics) or psoriasis (corticoids, calcipotriol, calcitriol, tazarotene, cade oil, acitretin, PUVA-therapy) or drugs or hyperlipemic drugs (or foodstuffs) and/or hypolipemic drugs (or foodstuffs). Among both of the latter types of drugs, it is possible to mention drugs based on sulfonylureas and glinides, drugs based on inhibitors of alpha-glycosidases, drugs based on biguanides (metformine), drugs based on activators of insulin sensitivity or thiazolidinediones (TZD, pioglitazone, rosiglitazone), which are PPAR agonists, hypolipemic drugs of the statin family or fibrate family (PPARα agonists), orlistat (Xenical) and sibutramine (Réductyl or Sibutral).

The anti-fat nutrients which may be used in association, are advantageously selected from the group formed by nutrients blocking absorption of fats, such as chitosan, nutrients capable of increasing thermogenesis ("fat burner") such as ephedrine (Ma Huang Chinese herb), caffeine, theine, and citrus aurantium, nutrients capable of controlling appetite ("appetite suppressors") such as L-phenylalanine and L-tyrosine, nutrients capable of regulating glycaemia, such as minerals, for example chromium or vanadium or magnesium or the ayurvedic herb *Gymnema Sylvester*, inhibitors of lipogenesis, such as hydroxycitric acid extracted from *Garcinia cambodgia* and nutrients capable of transporting fats, such as L-carnitine.

Examples of foodstuffs and of hyperglycemic therapies for rebalancing glycaemia, are antiretroviruses, glucocorticoids, immunosuppressors, IFN-Alpha, sexual steroids, THS, the pill, growth hormones, sympathomimetic agents, cardiovascular drugs, diuretics, beta-blocking agents, calcium inhibitors, psychotropic substances.

The anti-inflammatory agents which may used in association, are advantageously steroid anti-inflammatory agents (AIS), such as corticoids or non-steroid agents (AINS).

The immunomodulators which may be used in association, are advantageously tacrolimus, pimecrolimus, and oxazolines. The oxazolines which may be used in association, are advantageously oxazolines selected from the group formed by 2-undecyl-4-hydroxymethyl-4-methyl-1,3-oxazoline, 2-undecyl-4,4-dimethyl-1,3-oxazoline, (E)-4,4-dimethyl-2-heptadec-8-enyl-1,3-oxazoline, 4-hydroxymethyl-4-methyl-2-heptadecyl-1,3-oxazoline, (E)-4-hydroxymethyl-4-methyl-2-heptadec-8-enyl-1,3-oxazoline, 2-undecyl-4-ethyl-4-hydroxymethyl-1,3-oxazoline. Even more advantageously, said oxazoline is 2-undecyl-4,4-dimethyl-1,3-oxazoline, called OX-100 or Cyclocéramide®.

Hypopigmentary agents which may be used in association, are hydroquinone and its derivatives, arbutin, retinoic acid, retinol, retinaldehyde, kojic acid, azelaic acid, vitamin B3 or PP, resorcinol derivatives, resveratrol, licorice or white mulberry extracts, alpha-lipoic acid, linoleic acid, cation-chelating agents such as EDTA (ethylenediamine tetraacetic acid), soya bean extracts. Sepiwhite® (N-undecylenoyl-L-phenylalanine) marketed by Seppic, which is also a depigmentary cosmetic agent, may also be mentioned.

As an example of pigmentary agents, mention may notably be made of
  agents which color the skin: dihydroxyacetone, melanins;
  agents which stimulate the natural pigmentation process:
    psolarenes (8-methoxypsolarene, 5-methoxypsolarene, 4,5',8-trimethylpsolarene or vegetable extracts of *Psorelea corylifolia* and *Ammi majus*), carotenoids (lycopene, canthaxanthin), agents stimulating the cyclic AMP route (1. analogs of AMPc, such as 8-bromo-AMPc or dibutyryl-AMPc, 2. forskolin, 3. isobutyl-methyl-xanthin or theophyllin), activators of kinase C proteins (diacylglycerols, in particular oleyl-acetyl-glycerol), aliphatic or cyclic diols (1,2-propanediol, 5-norbornane-2,2-dimethanol, norbornane-2,2-dimethanol), monoterpene bicyclic diols, tyrosine derivatives (L-tyrosine, L-DOPA), dimethylsulfoxide, lysomotropic agents, thymidine dinucleotides, DNA fragments, analogs of the melanocyte-stimulating hormone, 3-isobutyl-1-methylxanthin, nitric acid donors (Brown, Journal of Photochemistry and Photobiology B: biology 63 (2001) 148-161);
  vegetable extracts, in particular algae, demonstrating a promelanogenic activity: *Laminaria digitata* (Thalitan of Codif).

The natural plant extracts which may be used in association, are advantageously extracts of avocado, lupin, soya bean or sunflower, maize and rapeseed or even maca. Mention may notably be made of avocado sugars (cf. international application WO 2005/115421), or avocado peptides (cf. international application WO 2005/105123).

The compounds containing unsaponifiables of vegetable oils, which may be used in association, are advantageously selected from the group formed by avocado furanic lipids, avocado and soya bean unsaponifiables, concentrates of lupine oil, concentrates of sunflower, maize and rapeseed oil and their mixtures.

Avocado furanic lipids which may be used in association, are advantageously natural 2-alkyl furanes, notably the active product Avocadofurane® marketed by Laboratoires Expanscience, which may be obtained by the method described in international application WO 01/21605.

The avocado and soya bean unsaponifiables which may be used in association, are advantageously a mixture of furanic avocado unsaponifiables and of soya bean unsaponifiables, in a respective ratio of about 1/3-2/3. The avocado and soya bean unsaponifiables are even more advantageously the product Piasclédine®, marketed by Laboratoires Expanscience.

Lupine oil concentrates which may be used in association, are advantageously concentrates obtained by molecular distillation of lupine oil, advantageously sweet white lupine oil, such as those described in international application WO 98/47479. They advantageously contain about 60% by weight of unsaponifiables.

Sunflower concentrates which may be used in association, are advantageously linoleic sunflower concentrates, such as the active product marketed by Laboratoires Expanscience, Soline® (cf. international application WO 01/21150).

"Sterol" unsaponifiables are unsaponifiables for which the sterol, methylsterol and triterpenic alcohol content is comprised between 20 and 95% by weight, preferably 45-65% by weight, based on the total weight of the unsaponifiable.

Hypoglycemic plants which may be used in association, are advantageously selected from the group formed by fenugreek (*Trigonella graenum*), corosolic acid (active compound of the leaves from the tree *Lagestroemia speciosa*), *Gymnema Sylvester*, fruit juice from bitter melon (*Momordica charantia*), eucalyptus (*Eucalyptus globulus*), *Panax ginseng*, blueberry leaves (*Vaccinum myrtillus*).

Oligo-elements which may be used in association, are advantageously selected from the group formed by magnesium, chromium, selenium, and their mixtures.

The composition according to the invention may be formulated as different preparations suitable for topical administration, oral, rectal, vaginal, nasal, auricular or bronchial administration, for parenteral administration.

According to a first alternative, different preparations are suitable for topical administration and include creams, emulsions, milks, ointments, lotions, oils, aqueous or water/alcohol or water/glycol solutions, powders, patches, sprays or any other products for external application.

According to a second alternative, the different preparations are suitable for oral administration; the *quinoa* extract being able to enter either a food composition or a food supplement. The food supplement may appear as a *quinoa* extract as such (for example a refined oil possibly enriched in its unsaponifiable fraction) or else as gelatin capsules or soft gelatin capsules or vegetable capsules within the scope of the present invention. Said food supplement may then contain from 10 to 100% by weight of *quinoa* extract.

According to this second alternative of the present invention, the *quinoa* extract of the present invention may be incorporated without any restriction into food, drinks, and nutraceuticals, included in those mentioned below:

1) dairy products: such as cheeses, butter, milk and other milk-based drinks, mixtures and spreads based on milk products, ice creams and yoghurts;

2) products based on fats such as margarine, spreads, mayonnaises, cooling fats, frying oils, and French dressings;

3) products based on cereals consisting of grains such as bread and pasta, whether the foodstuffs are cooked, oven-cooked or transformed;

4) confectionery such as chocolate, sweets, chewing gums, desserts, toppings, sherbets, icings, and other garnishes;

5) alcoholic or soft drinks, including sodas and other soft drinks, fruit juices, diet supplements, meal substitutes in the form of a drink like those sold under the name of BOOST™ and Ensure™ and;

6) various products such as eggs, transformed foodstuffs such as soups, ready-made sauces for pasta, prepared dishes and other products of the same kind.

The composition of the present invention may be directly incorporated and without any other modification into food, nutraceuticals, diet products notably hyperprotein products or drinks and this by means of techniques such as mixing, infusion, injection, mixing, absorption, kneading and spraying.

The administration modes, dosages and optimum galenic forms of the compounds and compositions according to the invention may be determined according to criteria generally taken into account in establishing a pharmaceutical treatment, in particular a dermatological or veterinary treatment adapted to a patient or an animal, such as for example the age or the body weight of the patient or the animal, the severity of his/her general condition, tolerance to the treatment, reported secondary effects, the type of skin. Depending on the desired type of administration, the composition and/or the active compounds according to the invention may further comprise at least one pharmaceutically acceptable excipient, notably a dermatologically acceptable excipient. According to the first alternative, an excipient is used which is adapted to administration via an external topical route. The composition according to the present invention may further comprise at least one adjuvant pharmaceutically known to one skilled in the art, selected from thickeners, preservatives, perfumes, dyes, chemical or mineral filters, moisturizing agents, hot springs, etc.

The composition comprising refined *quinoa* oil having the indicated specifications is particularly intended for cosmetic, dermatological or food use. Within the scope of a cosmetic or dermatological use, the composition will advantageously be formulated as a preparation suitable for topical administration. Within the scope of a use in food, with a nutritive or cosmetic purpose ("cosmet-food"), the composition will advantageously be formulated as a preparation suitable for oral administration. It may not comprise any excipient and may consist entirely of refined *quinoa* oil.

The composition comprising refined *quinoa* oil enriched in its unsaponifiable fraction is particularly intended for a cosmetic, dermatological or food use. Within the scope of a cosmetic or dermatological use, the composition will advantageously be formulated as a preparation suitable for topical administration. Within the scope of a food use, with a nutritive or cosmetic ("cosmet-food") purpose, the composition will advantageously be formulated as a preparation suitable for oral administration. It may not comprise any excipient and may consist entirely of refined *quinoa* oil concentrated in its unsaponifiable fraction.

The composition comprising an unsaponifiable is particularly intended for a cosmetic or dermatological use. The composition will advantageously be formulated as a preparation suitable for topical administration.

The composition comprising a peptide extract is particularly intended for cosmetic or dermatological use. The composition will advantageously be formulated as a preparation suitable for topical administration.

The object of the invention is also the use of *quinoa* extract, selected from a peptide or oside extract of *quinoa* or a lipid extract of *quinoa*, said *quinoa* lipid extract being itself selected from the group formed by an oil concentrated in its unsaponifiable fraction, an unsaponifiable or a refined oil having the specifications given in Table 2, for making a dermatological composition or a functional foodstuff.

A functional foodstuff is a conventional foodstuff, or which has the aspect of such a foodstuff, which belongs to normal food, and which has the characteristic of providing beneficial physiological effects exceeding its usual nutritional functions or of reducing the risk of chronic diseases.

The invention relates to a method of cosmetic treatment, of hygienic care, of beautification and/or a method for perfuming mucosas and/or normal, dry, fat, mixed, dehydrated, aged, sensitive, irritated, uncomfortable, intolerant skins, having a disequilibrium related to intrinsic, extrinsic or hormonal aging, or related to exogenous aggressions (pollutants, UV, stress . . . ), of allergic trend, having pigmentation disorders, having an unsightly aspect related to an excess load of fatty mass, characterized in that it consists of administering a composition or a functional foodstuff according to the invention.

The invention moreover relates to a method for treating integuments (hair, body hairs, nails) characterized in that it consists of administering a composition or a functional foodstuff according to the invention.

In particular, the composition or the functional foodstuff is intended for preventing and treating allergic, inflammatory, irritative pathologies or reactions or disorders of the barrier or homeostasia of skin, such as acne, atopical dermatitis, seborrheic dermitis, rosacea, psoriasis, vascular disorders, seat dermitis, sores, cracks, stings, cracks in particular of the breast, sunstrokes, inflammations due to rays of any kinds, irritations or allergies (by chemical, physical agents (tensile stress: pregnant women)), bacteriological, fungic or viral, parasitic (fleas, scabies, ringworm, acarids, dermatophytes), radiological or radiation (UV, IR) irritations or allergies or by innate immunity deficiency (anti-microbial peptides) or acquired immunity deficiency (cellular, humoral cytokins)), stretch marks and/or of mucosas (gingivitises (sensitive gingivitises of newborn, from hygiene, related to addiction to tobacco), parodontopathy, irritations of external or internal male or female genital spheres and/or immature, normal or mature integuments (alopecia, dandruff, hirsutisms, seborrheic dermitises).

The composition or the functional foodstuff may also be intended for tissue regeneration and for promoting healing, or may also be intended for protecting and strengthening the skin barrier, for regulating pigmentation disorders and for acting on lipolysis and lipogenesis mechanisms.

Refined *quinoa* oil, possibly concentrated in its unsaponifiable fraction, further has the following advantages: it allows a reduction in the risk of atherogenesis, it has hypocholesterolaemic properties, it acts in preventing certain cancers and cardiovascular diseases, in stimulating the immune response in elderly persons, in reducing the risk of cataract and in slowing down the progression of neurovegetative diseases.

Another advantage of refined *quinoa* oil, possibly concentrated in its unsaponifiable fraction, is that it may be used in cosmetics ("food-cosmetic"), more particularly with the purpose of improving skin aspect, for moisturizing the skin, preserving the condition of the skin barrier and of the intercorneocytary cement by providing essential fatty acids and sterols, in order to prevent skin aging by scavenging free radicals, and as a solar protective or anti-inflammatory agent.

According to a preferred alternative of the invention, refined *quinoa* oil, concentrated in its unsaponifiable fraction is used in treating disorders related to dermal tissue. Dermal connective tissue plays a major role as a support and sustainer at skin level, shock absorber, the dermis is notably responsible for firmness and flexibility. Degeneration of this tissue, associated with an alteration of the collagen network (collagens, in particular or type I, III, II and V) or elastic network (elastin—inhibition of synthesis, imperfect synthesis, degradation of collagen fibers, reduction in the number of fibroblasts and of their metabolism . . . ), may therefore have significant consequences on:

skin ageing (chronological, extrinsic ageing or photo-ageing and menopausal ageing), notably characterized by a reduction in the number and in the activity of fibroblasts, as well an excessive degradation of the extracellular matrix;

stretch marks, an affection of the fibroblast cell characterized by inflammation, inhibition of the expression of genes coding for fibronectin, collagens of type I and III and of elastin, transformation of fibroblasts into myofibroblasts under the effect of mechanical distensions. This degeneration of collagen tissue leads to the formation of an atrophic dermal scar. The main triggering factors are: inflammation and mechanical stress and hormonal environment (during pregnancy). Stretch marks affect about 50% of the young essentially female population. They are generally observed during pregnancy (60-70% of pregnant women), during puberty (25% of girls for 10% of boys), or during certain (metabolic, endocrine and infectious) diseases. These are linear, slightly depressed, narrow, lesions oriented in the direction of skin tension lines and covered with a folded epidermis. Their color varies according to the evolutive stage: they have red color, or even dark purple initially, and then assume a iridescent whitish aspect in a second phase;

deep wounds reach the dermis, they cause alteration of dermal tissue with a reduction in the number of fibroblasts and degradation of the matrix. The healing mechanism is set up in order to repair the altered tissue: fibroblasts proliferate and the extracellular matrix is remodeled: synthesis of the different components.

Another object of the invention is therefore the use of said oil enriched in unsaponifiables for preventing and/or treating skin aging, stretch marks, and deep wounds. Said oil enriched in unsaponifiables may also be used for promoting healing.

According to another advantageous alternative of the invention, said oil enriched in unsaponifiables may be used in preventing and/or treating subcutaneous atrophies of the dermis. Subcutaneous atrophies are a problem frequently encountered in dermatology. They may be secondary to different etiologies. Depending on their localization, these lesions represent a minor esthetical nuisance or on the contrary strongly handicap the person.

Subcutaneous atrophies may have different etiologies. At the first rank appear scar atrophies which are either post-traumatic (traumas right up to the dermis) or post-inflammatory (for example post-acne). Post-traumatic atrophic scars include epithelial atrophy with a linear basal membrane witnessing rearrangement of the dermo-epidermal junction with loss of the papillary pattern. Histologically, the thickness of the dermis is reduced, the collagen fibers are fine and fibrocytes are often more numerous than in normal skin. Dermal atrophy also includes hypotrophy of pilosebaceous and sometimes sudoral annexes. The scars from an inflammatory process are most often formed in the deep dermis and hypodermis. There is a thickening of the dermis which is accompanied by sclerosis. The constituents of the extracellular matrix are gradually replaced with thickened and dense collagen fibers. This sclerosis process is accompanied by a reduction in dermal vascularization and in the annexes. At this stage, one speaks of sclero-atrophy, a condition which may be observed in localized (morphed) scleroderma. This process may also affect the hypodermis in an immune (deep lupus, Perry-Romberg syndrome), drug-related (triteraphy, injection of corticoids), enzymatic (pancreatic cytosteatonecroses) or traumatic (atrophy of the hypodermis in women wearing thigh-high stockings) inflammatory context.

Other atrophies are listed: consecutive to local treatment with dermo-corticoids, consecutive to menopause and either associated or not with SHT (substitutive hormonal treatment), due to certain diseases, either genetic or not, hypoplasia, disease of the connective tissue of the skin of the collagen, Goltz syndrome, Pasini and Pierini atrophodermia, atrophiant pilary keratosis, finally during skin grafts, burns, losses of skin substances of any origins, bedsores.

The proposal is therefore to make up for the atrophy of the dermis by a treatment based on a *quinoa* concentrate (=Oil enriched in unsaponifiables) which reinitiates protein activity.

According to a preferred alternative of the invention, the peptide and oside extract of *quinoa* is used in epidermal healing.

A perturbation of the integrity of the skin may occur in several contexts. The skin may undergo damages during surgeries, burns, radiations, cuts, scratches, friction and pressure. The severity level of the wound varies depending on certain factors such as the extent, the depth and the nature. In order to maintain the essential function of the skin, it is very important to repair it when such an event occurs. The healing of a skin wound represents the whole of the processes which lead to closing of the wound and to functional recovery of the skin tissue. The epidermis heals by regeneration or re-epithelialization, i.e. it recovers its structure and its original functions. As it is incapable of reacting to a lesion by regeneration, the dermis heals by repair, i.e. the original tissue is replaced with non-specific connective tissue with as a result, the formation of a less functional scar (ex. Lower mechanical strength). These processes involve different cell populations, distinct cell compartments (epidermis and dermis), various mediators and multiple interactions between all these elements, the whole varying over time.

Re-epithelialization consists in regeneration by keratinocytes of an organized, pavimentous, stratified, keratinized epithelium which covers the wound and again forms a protective barrier against the external environment in order to reduce mortality as a result of a wound. The re-epithelialization mechanism is performed in 3 steps which occur in parallel but in a time-shifted way: (1) migration of the keratinocytes (cell migration may be influenced by several mechanisms, such as the loss of contact inhibition; the presence of inflammatory mediators such as growth factors, or proteins secreted by the cells, but also by the different contacts with substrates of the matrix such as fibronectin and laminin 5); (2) cell proliferation (a mitotic wave occurs for filling the space left by the migrating cells and for covering the lesion. Proliferation of the keratinocytes which occurs after 48-72 hours, does not seem to affect the migration. It is accomplished under the influence of many factors which may be secreted by the neighboring cells such as fibroblasts or by the keratinocytes themselves: KGF (Keratinocyte Growth Factor), IL-1, IL-6, IL-8, Colony Stimulating Factor (CSF), PDGF, TNF-a, IGF-1 (Insulinase Growth Factor), (3) maturation of the epidermis (maturation and differentiation of the epidermis occur simultaneously with closure of the wound and correspond to resumption of the function and normal morphology of the keratinocytes). The keratinocytes are activated, adapt their morphology to migration, migrate and proliferate under the influence of different growth factors for re-epithelializing the wound. With progression of the covering of the wound, the neo-epidermis begins its maturation in order to form a protective corneal layer.

Certain growth factors, which control migration of the keratinocytes, are also capable of influencing migration. This is the case of EGF and of TGF-β which stimulate it while increasing the expression of integrin α2β1 at the surface of the keratinocytes but also TGF-β which is one of the major factors involved in the migration and which acts by activating the matrix synthesis.

The cell-matrix interaction is significant during healing of the wound. Indeed, the extracellular matrix contains adhesive substances and fibers which guide the migrating cells. In the same way, molecules present in the blood may contribute to cell migration. For example, fibrin and fibronectin, are attached to the temporary matrix and form a structure on which the keratinocytes may migrate. The migrating keratinocytes also elaborate elements of this matrix. Keratinocytes synthesize laminin 5, collagen V and the antigen of bullous pemphigoid. The effect of the various substrates on the migration of keratinocytes is mediated by integrins and the secretion of protease of the extracellular matrix (MMP-1, MMp-2 and MMP-9), which successively allow them to adhere to and free themselves from these substrates.

Laminin 5 is a specific protein of the basal lamina of epithelia which have secretion or protection functions, such as the mucosas or skin. Laminin 5 is considered as the key component of the complex for anchoring the epidermis and as the protein which contributes the most to stability of the basal membrane. Laminin 5 results from the heterotrimeric assembly of α3, β3 and γ2 subunits and is exclusively synthesized by epithelial cells, as a precursor. The major role of laminin 5 is emphasized by the existence of hereditary or acquired diseases, resulting from an abnormality of synthesis and/or expression of one of its constitutive subunits. These diseases, called junctional bullous epidermolyses, notably lead to fragility of the dermo-epidermal junction of the skin characterized by spontaneous formation of epidermal bullae. Thus, laminin has a determining biological role since it allows adherence of the adjacent epithelial cells. In addition to its role in stable adherence, laminin 5 plays a significant role during cell migration since it is strongly expressed by the migrating keratinocytes in the earlier phases of epidermal healing. In normal skin, there is very little or no marking of laminin 5 in the cytoplasm of basal keratinocytes while in a healing wound, laminin 5 is detected in the basal cells. The long form of laminin 5 interacts with the α3β1 and α2β1 integrins which are two receptors, again found in focal adherence plates useful for cell movement. Integrin α2β1 seems to be involved predominantly in the migration of keratinocytes. During the migration, regulation of the expression of laminin 5 is mediated by TGF-β and INF-γ.

Skin healing is associated with migration and remodeling events of the matrix which have resorted to the action of matrix metalloproteases (MMPs). The keratinocytes therefore move through a temporary matrix which they degrade, if need be, for facilitating their migration and of which they will gradually modify the composition. The MMPs are a family of zinc-dependent enzymes with a very preserved structure and which have the capability of degrading the components of the extracellular matrix. They may be synthesized by different cell types at the skin (fibroblasts, keratinocytes, macrophages, endothelial, eosinophilic cells, Langerhans cells, . . . ). The predominant role of MMPs in the proteolytic remodeling of the extracellular matrix is now clearly established in skin healing. The effect of various substrates on the migration of keratinocytes is mediated by the secretion of protease of the extracellular matrix: MMP-1, MMP-2 and MMP-9, which successively allows them to adhere to and to free themselves from these substrates. MMP-9 is expressed predominantly during skin healing and is involved in the migration and matrix remodeling phase. This protease will also be a major element of healing without any scars.

Now, it has been shown that the extract for promoting healing according to the invention directly acts on the first 2 steps involved in re-epithelialization (cell migration and proliferation).

Stimulation of the migration of keratinocytes:
Action on the expression of the genes coding for the 3 chains making up laminin 5 ($\alpha3\beta3\gamma2$);
Action of the synthesis of MMP-9 via an increase in the expression of its gene;
Action on the migration of keratinocytes
Stimulation of the proliferation of keratinocytes:
Direct action on cell proliferation
Indirect action of the fibroblasts: secretion of more KGF: a growth factor activating cell division of keratinocytes.

Thus, the object of the invention is the use of a peptide and oside *quinoa* extract, as described earlier for promoting healing. In particular, said peptide and oside extract may be used for preventing and/or treating surface scars such as: post-acne scars, post-peeling scars, post-laser scars, post-burn scars, and scratches. Said peptide and oside extract may also be used as a care product (cosmetic) for fragile lips and cheilitises. Said peptide and oside extract may also be used in preventing skin ageing, because of a lack of healing with age. This peptide and oside extract may also be used in treating and/or preventing stretch marks.

This peptide and oside extract may also be used for repairing the skin after stings (mosquitoes). It also allows repair of abrasion of the skin by physical mechanisms (scratching, prurit, mechanical friction, laser radiation), by chemical and biochemical mechanisms (peeling, erythema of the buttocks, for example). In particular, this extract may be used in the cosmetic treatment of spots and/or crusts, allowing repair of the skin after spots due to pathologies such as acne or chicken poxes, and/or crusts due to pathologies (atopy, milk crusts).

This peptide and oside extract also founds application in the cosmetic treatment of fragile and sensitive skins.

The examples which follow illustrate the invention but are non-limiting.

Example 1

Refined *Quinoa* Oil (Deodorized): Preparation Method and Specifications

Refined *quinoa* oil is obtained by extraction with a solvent (n-hexane) of *quinoa* grains (1,000 kg, 5.5% yield) and by obtaining raw *quinoa* all (55 kg). This raw oil is then refined (70% yield) in order to lead to refined *quinoa* oil (38.5 kg). A cloudy all of yellow color is obtained with a deposit; no traces of hexane are found.

Deodorized refined *quinoa* all has the following specifications:
Peroxide number: 7.3 meq/kg; acid number: 0.30 mg KOH/g.
Fatty acid composition: C14 0.1%; C16 8.2%; C16' 0.2%; C18 0.8%; C18' 30.4%; C18" 47.2%; C18'" 8.3%; C20 0.6%; C20' 1.7%; C22 0.7%; C22' 1.6%; C24 0.2%.
Total tocopherol content: 4.8 mg/100 g
Relative % of $\alpha$-tocopherol: 22.3%; relative % of $\beta$-tocopherol: 0.0%; relative % of $\gamma$-tocopherol: 61.5%; relative % of $\delta$-tocopherol: 16.2%.
Total sterol content: 1.63 g/100 g
Relative % of campesterol: 1.53%; relative % of stigmasterol: 3.19%; relative % of $\beta$-sitosterol: 20.00%; relative % of $\delta$-5-avenasterol: 1.7%; relative % of $\delta$-7-stigmasterol: 46.35%; relative % of $\delta$-7-avenasterol: 8.55%
Squalene content: 2.5 g/100 g

Example 2

Refined *Quinoa* Oil Concentrated in its Unsaponifiable Fraction (=*Quinoa* Oil Concentrate): Preparation Method and Specifications Refined *quinoa* oil (deodorized, 38.5 kg) is subject to a molecular distillation step in order to lead to a refined *quinoa* oil concentrated in its unsaponifiable fraction, further designated as *quinoa* oil concentrate (3.85 kg, 10% yield).

The deodorized refined *quinoa* oil concentrated in its unsaponifiable fraction has the following specifications:
Cloudy oil of yellow color with deposit; no traces of hexane are found.
Peroxide number: 1.43 meq/kg; acid number: 3.04 mg KOH/g.
Fatty acid composition: C14 0.3%; C16 12.4%; C16' 0.30; C18 0.7%; C18' 29.4%; C18" 47.1%; C18'" 7.7%; C20 0.3%; C20' 0.9%; C22 0.3%; C22' 0.6%; C24 0.1%.
Total tocopherol content: 58.7 mg/100 g
Relative % of $\alpha$-tocopherol: 72.3%; relative % of $\beta$-tocopherol: 0.7%; relative % of $\gamma$-tocopherol: 23.1%; relative % of $\delta$-tocopherol: 4.0%.
Free sterol content: 0.4 g/100 g
Total sterol content: 7.73 g/100 g
Relative % of campesterol: 5.57%; relative % of stigmasterol: 3.4%; relative % of $\beta$-sitosterol: 26.84%; relative % of $\delta$-5-avenasterol: 2.3%; relative % of $\delta$-7-stigmasterol: 39.48%; relative % of $\delta$-7-avenasterol: 5.97%
Squalene content: 16.8 g/100 g

Example 3

*Quinoa* Peptide and Oside Oil: Preparation Method and Specifications

A *quinoa* peptide and oside extract was prepared according to the following procedure:
Initial raw material: *quinoa* cake, with 10-12% of proteins by weight based on the dry material weight (DM=dry material). This *quinoa* cake is subject to alkaline extraction (adjustment of the pH to pH 10. The supernatant is then subject to ultrafiltration by means of 8 kDa mineral membranes (protein enrichment). Next, the retentate is subject to a concentration step before the enzymatic hydrolysis step. Enzymatic hydrolysis of the proteins is carried out with the Prolyve 1000, at a temperature of 55° C., at a pH of 8. At the end of the enzymatic hydrolysis step, the enzyme is deactivated by heat treatment. The hydrolysate is then subject to an ultrafiltration step with 8 kDa mineral membranes (recovery of peptides in the filtrate). The ultrafiltrate is concentrated and then optionally subject to sterilizing 0.2 μm filtration and/or freeze-dried.

The peptide and oside *quinoa* extract has the following specifications:
A powder of orange-yellow color without preservatives
Composition with respect to the powder (%, w/w)
    α-aminated nitrogen (OPA, leucine equivalent): 13%±20%
    Proteins (biuret, BSA equivalent): 27%±20%
    Total sugars (anthrone, glucose equivalent): 24%±20%

TABLE 5 distribution profile of the molar masses of the peptides and amino acids

| Molar mass (Da) | >3,500 | 3,500-1,200 | 1,200-300 | 300-130 | <130 |
|---|---|---|---|---|---|
| Peptide distribution (%) | 2 | 15.5 | 44.5 | 15 | 23 |

Example 4

Refined *Quinoa* Oil Concentrated in its Unsaponifiable Fraction (=*Quinoa* Oil Concentrate): Biological Activities The effect of *quinoa* oil concentrate, obtained in Example 2, was evaluated on different parameters of the dermal matrix: (a) effect on proliferation of fibroblasts, (b) effect on the extracellular matrix of the dermis: genic expression of collagen I, collagen III and elastin, (c) effect on mechanical distension of the dermis: effect on the isometric forces developed by fibroblasts from red stretch marks.

Material and Methods:
a. Study of the Proliferation of Dermal Fibroblasts

The MTT [3-(4,5-dimethylthiazol-2-yl)-2,5-diphenyl-tetrazolium bromide] test is a colorimetric test which measures cell viability. MTT is a water-soluble tetrazolium salt of yellow color; metabolically active cells are capable of reducing it into blue formazan crystals.

On D0, the fibroblasts are sown in an RPMI medium with 1% SVF in a 96-well plate. On D1, the cells are treated with the *quinoa* oil concentrate in RPMI medium with 1% SVF, with 0.005% and 0.01% of dry material (DM) or with RPMI medium with 10% SVF (positive control) for 24 and 48 hours.

At the end of the treatment, cell viability is quantified by an MTT test: after 3 hours of contact with MTT, the formed formazan crystals are solubilized by DMSO and the optical density proportional to the amount of metabolically active, therefore live, cells, is read at 570 nm versus the blank (wells without cells).

b. Study of the Effect of *Quinoa* Peptides on the Expression of Genes Coding for Collagen I and Collagen III and Elastin by RT-PCR b.1. Principle of Real Time Quantitative PCR:
Real time quantitative PCR or QRT-PCR (Quantitative Real Time Polymerase Chain Reaction) is a molecular biology method, which allows specific and quantitative measurement of the expression of genes of interest by amplification. Quantification is based on tracking the amplification of genes in real time by using as a reporter system, SYBR Green technology: a molecule with fluorescent properties which is inserted inside the double strand DNA. PCR takes place in a succession of temperature cycles according to 3 steps:
    Denaturation: separation of 2 DNA strands.
    Hybridization: recognition of a DNA sequence corresponding to a target gene by means of specific primers.
    Extension: of the sequence of interest by a action of a polymerase.

At the end of the reaction, quantification is achieved by analyzing the "threshold cycle" (Ct=point where the fluorescence initial signal will be statistically and significantly higher than the background noise). DNA amounts are compared in the exponential part, moment during which the increase in the DNA amount is proportional to the initial matrix amount.

b.2. Procedure:
On D0, the fibroblasts were sown on 6-well plates in RPMI medium added with 10% SVF. On D1, the fibroblasts were treated with TGF β1 at 5 ng/mL or the *quinoa* oil concentrate with 0.005% and 0.01% DM in RPMI medium with 1% SVF for 48 hours. At the end of the treatment of the cells, the total DNAs were extracted (extraction kit RNeasy kit MiniKit; Qiagen) and then assayed quantitatively in minichips by means of an Experion system (Experion RNA StdSens kit; Biorad). Total RNAs are then back-transcribed into cDNA (iScript cDNA Synthesis kit; Biorad). Finally the neo-synthesized cDNAs relative to the genes of interest (collagen I, collagen III, elastin) or to reference genes (HPRT, GAPDH, YWHAZ, beta actin=normalizers) were selectively amplified with real time PCR (iQ5, Biorad) by using specific primers of the target sequences.

The expression of the reference genes is analyzed in the same samples as those for which expression of the genes of interest is evaluated in order to normalize the results and to make sure that they are actually the results of the effect of the treatment by *quinoa* oil concentrate.

b.3. Analysis of the Results:
The results are normalized with respect to the most stable reference gene (according to the geNorm algorithm): DCt=gene of interest Ct−most stable reference gene Ct.

The variation in the number of copies of the genes of interest during the treatment is then calculated according to the following formula: DDCt=control DCt−treatment DCt.

Finally, the relative amount or the expression level of the genes of interest, normalized by the expression level of the reference genes in the untreated and treated samples is obtained by the formula: QR=2DDCt c. Evaluation on the Effect of the Isometric Forces Developed by Fibroblasts from Red Stretches
c.1. Presentation of the GlaSbox® System Mechanical inhibition of collagen gel in which the fibroblasts are included is expressed by the generation of a force, called <<a retraction force>> or <<an isometric force>>.

The lattices develop in a culture dish which consists of 8 rectangular containers. In each of them, two flexible silicon blades are immersed, the lower portions of which consist of grids on which the lattice adheres during its polymerization. The lattice develops between both blades in order to result in a rectangular shape slightly shrinked at the centre. This shape in conventional mechanics is designated as a bobbin shape. These blades are equipped at their upper portion with a strain gauge system covered with gold wires deposited at their surface. Under the influence of the retraction force developed by the fibroblasts, the silicon blades deform. This is expressed by a variation in the electric resistance value of the strain gauge, measured via a Wheatstone bridge. This variation indicates the force developed within the lattice, measured in real time by means of a PC acquisition card and a suitable software package.

c.2. Preparation of Equivalent Tensioned Dermises and Measurement of Isometric Forces A medium for making lattices is prepared by mixing: 6 volumes of culture medium with 3 volumes of rat tail collagen I (2 mg/mL) and one volume of cell suspension (8.105 cells/mL). The mixture is poured into the rectangular containers of the GlaSbox. Within a few minutes at 37° C., a gel is formed. The different media either containing or not the active ingredient are added. The isometric forces will be measured for 48 hours. At the end of the handling, the collagen lattices are detached and digested in a collagenase solution. After 2 hours of incubation at 37° C., the cells inside each collagen lattice are counted. The forces are expressed as the number of cells after 48 hours of handling.

c.3. Statistical analysis: the values are expressed by the mean±the standard error of the distribution of means (sem). A 2 factor variance analysis was performed.

Results a. Proliferation of the Fibroblasts:

the treatment of the fibroblasts by the *quinoa* oil concentrate with 0.005 and 0.01% DM, significantly stimulates the proliferation in a dose-dependent way (respectively: +17 and +23% increase relatively to the control without any treatment, after a treatment for 48 hrs).

TABLE 6

Study of proliferation of fibroblasts in the presence of quinoa oil concentrate

| | 24 hr treatment | | | 48 hr treatment | | |
|---|---|---|---|---|---|---|
| | Mean DO (optical density) MTT | % increase | Student t test | Means DO MTT | % increase | Student t test |
| Control | 0.754 | 100 | | 0.675 | 100 | |
| Positive control (RPMI-10% SVF) | 0.900 | 119 | P < 0.01 | 1.249 | 185 | P < 0.01 |
| quinoa oil concentrate (0.005%) | 0.769 | 112 | P < 0.05 | 0.753 | 117 | P < 0.01 |
| quinoa oil concentrate (0.1%) | 0.843 | 120 | P < 0.01 | 0.793 | 123 | P < 0.05 | b. Expression of Collagen I:

the quantitative analysis of expression kinetics of mRNA of collagen I was performed by quantitative PCR (Q-PCR) after 48 hours of incubation with TGF-β1 at 5 ng/mL. The obtained results indicate significant induction of the expression of the gene for collagen I (Table 7). The *quinoa* oil concentrate also stimulates in a dose-dependent way the expression of collagen I (+58 and +67%).

TABLE 7

Study of genic expression of collagen I

| | Mean dCt | ddCt | QR | % of induction |
|---|---|---|---|---|
| Control | −2.3 | 0.00 | 1.00 | |
| TGFβ at 5 ng/mL | −3.2 | 0.9 | 1.87 | 87 |
| quinoa oil concentrate 0.005% | 2.96 | 0.66 | 1.58 | 58 |
| quinoa oil concentrate 0.01% | −3.04 | 0.74 | 1.67 | 67 | c. Expression of Collagen III:

On the other hand, the effect of *quinoa* oil concentrate on the expression of the gene of collagen III was analyzed. The results shown in Table 8, demonstrate significant increase in the expression of the gene for collagen III (+92 and +62%).

TABLE 8

Study of genic expression of collagen III

| | Mean dCt | ddCt | QR | % of induction |
|---|---|---|---|---|
| Control | 4.92 | 0.00 | 1.00 | |
| TGFβ at 5 ng/mL | 2.51 | 2.4 | 5.27 | 427 |
| quinoa oil concentrate 0.005% | 3.97 | 0.94 | 1.92 | 92 |
| quinoa oil concentrate 0.01% | 4.22 | 0.69 | 1.61 | 62 | d. Expression of Elastin:

an effect of the *quinoa* oil concentrate was also demonstrated on the expression of the gene for elastin (Table 9), with an induction of +96 and +67% relatively to the control without any treatment.

TABLE 9

Study of genic expression of elastin

| | dCt | ddCt | QR | % of induction |
|---|---|---|---|---|
| Control | 4.58 | 0.00 | 1.00 | |
| TGFβ at 5 ng/mL | 2.16 | 2.4 | 5.35 | 435 |
| quinoa oil concentrate 0.005% | 3.61 | 0.97 | 1.96 | 96 |
| quinoa oil concentrate 0.01% | 3.84 | 0.74 | 1.67 | 67 | e. Study of the Effect of *Quinoa* Oil Concentrate on the Contractile Forces Developed by Fibroblasts of Red Stretch Marks within an Equivalent Tensioned Dermis in the GlaSbox® System.

Figure 2A:
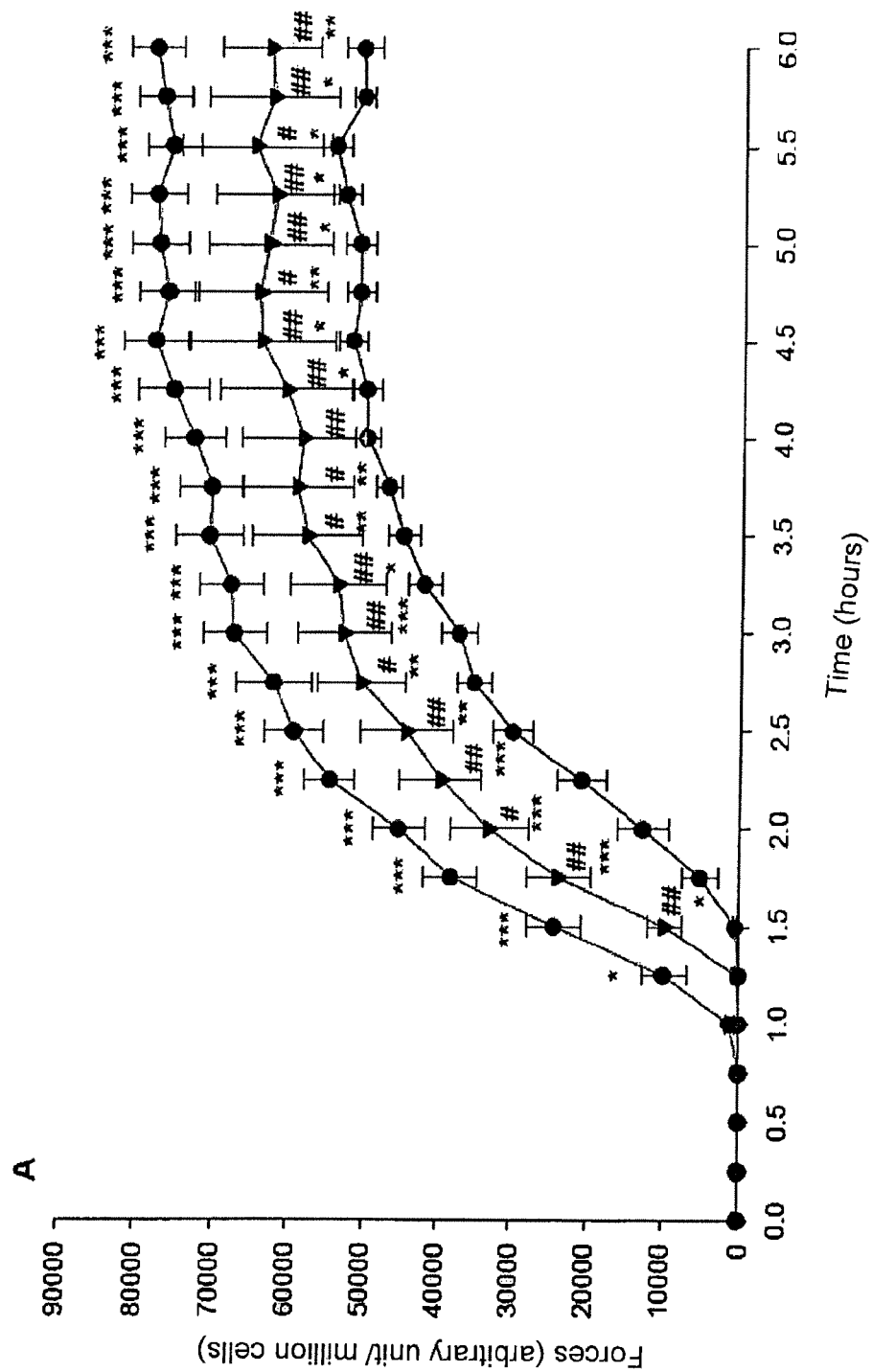
Figure 2B:
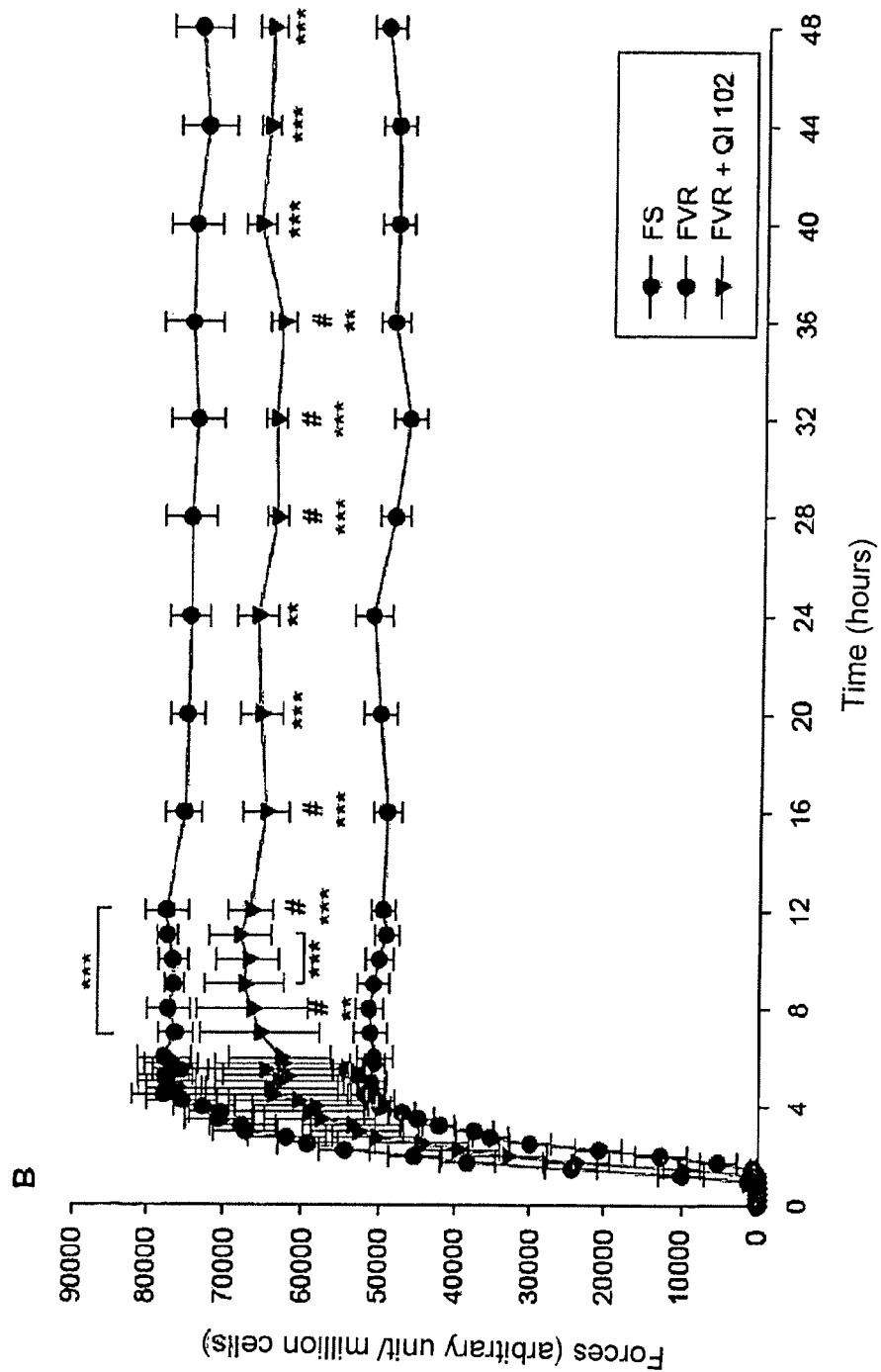

As shown in FIG. 2, addition of 0.01% of *quinoa* oil concentrate to the culture medium significantly reduces the contractile forces developed by the fibroblasts or red stretch marks after 1 hr 30 min of culture and this right up to the 36$^{th}$ hour. The curves obtained during this study consist of 3 distinct phases:

Phase I: the isometric force remains weak for the first two hours of culture. This phase corresponds to polymerization of the collagen gel.

Phase II: the isometric force increases quasi linearly up to a maximum, with a mean value during the first six to eight hours of culture. This phase corresponds to the time required for the fibroblasts for extending and adhering to the collagen fibers.

Phase III: the isometric force is maintained during the culture time. This phase corresponds to rearrangement of the collagen matrix by the fibroblasts and to increase in the expression of integrin α2β1.

The *quinoa* oil concentrate has a relaxing effect which is maintained over time because it reduces the isometric forces developed by the fibroblasts from the red stretch marks both during phase II and phase III of the curve.

FIG. 2: Contractile forces developed within an equivalent tensioned dermis in the GlaSbox® system during 48 hours of culture (B) (A: detail of the first 6 hours) (mean±sem) in the presence or in the absence of *quinoa* oil concentrate (QI102). (*$p<0.05$; $p<0.01$ and *$p<0.001$ versus FS [Healthy Fibroblasts]; #$p<0.05$ and ##$p<0.01$ versus FVR [fibroblasts of red stretch marks]).

Conclusion

The investigations shown here have made possible a demonstration of the role of *quinoa* oil concentrate on the regulation of dermal tissue. Indeed, it was shown that the *quinoa* oil concentrate causes: (a) stimulation of the proliferation of fibroblasts, (b) induction of the expression of collagen I, collagen III and elastin by fibroblasts; (c) modification of the mechanical properties of fibroblasts of red stretch marks: a transient and long term relaxation effect.

By stimulating the synthesis of the different components of the extracellular matrix, the *quinoa* oil concentrate may play a significant role in restoring and regulating dermal homeostasia in the case of alteration (aged, aggressed skin, stretch marks, scars . . . ).

Example 5

Peptide and Oside *Quinoa* Extract (=*Quinoa* Peptide): Biological Activities

The activity of the *quinoa* peptides obtained in Example 3 was evaluated on the first 2 mechanisms involved in skin re-epithelialization (evaluation at two concentrations: 0.05% DM and 0.1% DM):

migration of keratinocytes: (i) evaluation of the effect on the expression of the genes composing laminin 5, (ii) evaluation of the effect on the expression and on the synthesis of MMP-9 and (iii) evaluation of the functional effect on the migration of keratinocytes proliferation of keratinocytes: (i) evaluation of the effect on proliferation of keratinocytes, (ii) evaluation of the effect on the synthesis of KGF by fibroblasts.

Material and Methods a. Study of the Effect of *Quinoa* Peptides on the Expression of Genes Coding for Laminin 5 and PPM-9 by RT-PCR Principle of real time quantitative PCR: cf. Example 4

Procedure:

On day 0, the keratinocytes were sown in 24-well plates in a KGM-2 medium. On D1, the cells were treated with TGFβ1 at 5 ng/mL or *quinoa* peptides with 0.05 and 0.1% DM for 48 hours. At the end of the treatment of the cells, the total RNAs were extracted (RNeasy MiniKit extraction kit; Qiagen) and then quantitatively assayed in minichips by means of the Experion system (Experion RNA StdSens kit; Biorad). The total RNAs were then backtranscribed into cDNA (iScript cDNA Synthesis kit; Biorad). Finally, the neo-synthesized cDNAs relative to the gene of interest (genes coding for the 3 chains making up laminin 5: α2β3δ2 and MMP-9) or to the reference genes (HPRT, GAPDH, YWHEZ, beta actin=normalizers) were selectively amplified by real time PCR (iQ5, Biorad) by using specific primers of the target sequences.

The expression of the reference genes is analyzed in the same examples as those for which the expression of the genes of interest is evaluated in order to normalize the results and to make sure that they are actually the result of the effect of the treatment by *quinoa* peptides.

Analysis of the results: the results are normalized with respect to the most stable gene, cf. Example 4 b. Study of the Migration of Keratinocytes

Plastic culture supports are coated with collagen I; a control support is coated with gelatine (migration on gelatine is clearly less than on native collagen). The keratinocytes were sown in coated dishes and non-adherent cells were removed after 6 hours of incubation at 37° C. and with 5% $CO_2$. The culture medium was then replaced by medium either containing or not 0.1% *quinoa* peptides. After one night of incubation, the cell divisions were blocked by incubation for 2 hours with a solution of mitomycin C. An artificial, reproducible scar was produced on cell mats and after washings, the treatment was renewed. After 48 hours, the cells were fixed and the nuclei were marked with the fluorescent dye from Hoechst.

Digitized images were taken every day. An analysis of the migration of the keratinocytes is carried out between the image captured at instant D0 (allowing selection of the artificial scar) and the "Hoechst" image captured at D2 allowing the number of migrating cells to be counted.

c. Study of the Proliferation of Keratinocytes by the MTT Method

On D0, the keratinocytes are sown in a KGM2 medium day1, the cells are treated with trans-retinoic acid (ATRA) at 1 μM or *quinoa* peptides with 0.05% and 0.1% DM for 24 and 48 hours. At the end of the treatment, cell viability is quantified by an MTT test: after 3 hours of contact with MTT, the formed formazan crystals are solubilized by DMSO and the optical density, proportional to the amount of metabolically active cells therefore live cells, is read at 570 nm against the blank (wells without any cells).

d. Dosage of MMP-9 Secreted by Keratinocytes.

The keratinocytes were sown in 24-well plates; after 24 hours in incubation at 37° C., with 5% $CO_2$, the cells were treated with *quinoa* peptides with 0.05% and 0.01% DM. TGFβ tested at 5 ng/mL was used as a positive control. After 48 and 72 hours of treatment, the amount of MMP-9 secreted by the cells was assayed in the culture supernatant by means of an ELISA kit (R&D Systems), according to the procedure recommended by the supplier. In parallel, the amount of living cells per well was determined by a colorimetric neutral red test: optical density OD, proportional to the amount of living cells, is read at 570 nm.

The amount of MMP-9 is expressed in living cells: (ng/mL)/OD570 (optical density at 570 nm) MTT.

e. Dosage of KGF Secreted by Fibroblasts

The fibroblasts were sown in a 24-well plate in RPMI at 1% SVF; after 24 hours of incubation at 37° C., with 50 $CO_2$, the cells were treated with *quinoa* peptides with 0.05% and 0.01% DM. IL1α (Sigma) at 100 ng/mL was used as a positive control. After 24 and 48 hours of treatment, the amount of KGF salted out by the fibroblasts was assayed with an ELISA kit (R&D Systems), according to the procedure recommended by the supplier. In parallel, the amount of living cells per well was determined by a colorimetric neutral red test: optical density OD, proportional to the amount of living cells, is read at 570 nm. In parallel, the amount of living cells per well was determined by an MTT colorimetric test: optical density OD, proportional to the amount of living cells, is read at 570 nm.

The amount of KGF is expressed by the living cells: pg/mL/OD570 MTT.

f. Statistics:

the Significance of the Results was Evaluated by a Student t Test.

Results a. Expression of the Heterotrimer α3β3δ2 of Laminin 5

The genic control of the re-epithelialization process involves several transcription or growth factors, in particular TGF-β1 which is released during the first instants following an injury. Under the physiological conditions of re-epithelialization, it was demonstrated that TGF-β1 stimulated expression of laminin 5. This growth factor is used as a positive control in order to study genic expression of this protein, in order to approach physiological conditions.

Quantitative analysis of the kinetics of expression of mRNAs of the different chains making up laminin 5 was achieved by quantitative PCR-Q-PCR) after 48 hours of incubation with TGF-β1 at 5 ng/mL. The obtained results indicate very significant induction of the expression of the 3 investigated genes (p<0.01), and with induction factors reaching 12 for α3 and up to 17 for ±γ2 (Table 10: A/B/C). mRNA β3 was also induced at a lower level, of the order of 5 times.

The potential implication of *quinoa* peptides in the regulation of the expression of the 3 genes making up laminin 5 was investigated. The obtained result show that the *quinoa* peptides significantly stimulate in a dose-dependent way the expression the genes, the induction factors attain 3 for the α3 chain, 2 for the β3 chain and 2.6 for the γ2 chain.

TABLE 10 genic expression of the 3 chains making up laminin 5.

| | Mean dCt | Standard Deviation | p | ddCt | QR | % of induction |
|---|---|---|---|---|---|---|
| Genic expression of the α-3 chain of laminin 5 | | | | | | |
| Control | 1.435 | 0.659 | | 0.00 | 1.00 | |
| TGFβ at 5 ng/ml | −0.944 | 0.664 | p < 0.01 | 3.69 | 12.93 | 1193 |
| quinoa peptides 0.05% | 0.446 | 0.685 | p < 0.01 | 1.49 | 2.82 | 182 |
| quinoa peptides 0.1% | 0.466 | 0.578 | p < 0.01 | 1.64 | 3.12 | 212 |
| Genic expression of the β-3 chain of laminin 5 | | | | | | |
| Control | 1.435 | 0.659 | 0.00 | 0.00 | 1.00 | |
| TGFβ at 5 ng/ml | −0.944 | 0.664 | p < 0.01 | 2.38 | 5.20 | 420 |
| quinoa peptides 0.05% | 0.446 | 0.685 | p < 0.01 | 0.99 | 1.98 | 98 |
| quinoa peptides 0.1% | 0.466 | 0.578 | p < 0.01 | 0.97 | 1.96 | 96 |
| Cenic expression of the γ-2 chain of laminin 5 | | | | | | |
| Control | 2.225 | 0.418 | | 0.00 | 1.00 | |
| TGFβ at 5 ng/ml | −1.925 | 0.453 | p < 0.01 | 4.15 | 17.76 | 1676 |
| quinoa peptides 0.05% | 1.502 | 0.489 | p < 0.01 | 0.72 | 1.65 | 65 |

TABLE 10-continued genic expression of the 3 chains making up laminin 5.

| | Mean dCt | Standard Deviation | p | ddCt | QR | % of induction |
|---|---|---|---|---|---|---|
| quinoa peptides 0.1% | 0.839 | 0.336 | p < 0.01 | 1.39 | 2.61 | 161 | b. Study of the Expression of MMP-9.

Among the matrix proteases involved in re-epithelialization, MMP-9 plays a particularly significant role. It is positively regulated by TGF-β1 and pro-inflammatory cytokines, but it is also expressed on the wound site by the migrating keratinocytes.

As shown in Table 11, the analysis of the results of Q-PCR allows an earlier induction of the expression of the gene of MMP-9 with a factor 8 to be observed after 48 hours of stimulation by TGF-β. By using this model, the effect of *quinoa* peptides on the migration of keratinocytes was also shown, through their action on the expression of the MMP-9 gene. Thus, the *quinoa* peptides significantly stimulate the expression of MMP-9 by a factor 2.6 relatively to the control without any treatment.

TABLE 11

Study of the genic expression of MMP-9

| | Mean dCt | Standard Deviation | p | ddCt | QR | % of induction |
|---|---|---|---|---|---|---|
| Control | 6.08 | 0.84 | | 0.00 | 1.00 | |
| TGFβ at 5 ng/ml | 3.07 | 0.55 | p < 0.01 | 3.01 | 8 | 807 |
| quinoa peptides 0.05% | 5.06 | 0.57 | p < 0.01 | 1.02 | 2 | 100 |
| quinoa peptides 0.1% | 4.68 | 0.74 | p < 0.01 | 1.4 | 2.63 | 163 | c. Study of the Production of MMP-9 Protein

After having investigated the profile of genic expression of MMP-9 in the presence of *quinoa* peptides, it was verified that induction of the expression of the gene also increases secretion of the protein. The influence of *quinoa* peptides on the synthesis and secretion of MMP-9 by keratinocytes, after a treatment of 48 and 72 hours, was therefore evaluated. The results are shown in Table 12. Thus, *quinoa* peptides significantly increase the amount of MMP-9 secreted by keratinocytes (an increase ranging up to 55%).

TABLE 12

Dosage of MMP-9 protein in the supernatants of keratinocytes.

| | Treatment 48 h | | | Treatment 72 h | | |
|---|---|---|---|---|---|---|
| | Amount of MMP-9* | % A | Student t test | Amount of MMP-9* | % A | Student t test |
| Control | 2.458 | | | 2.207 | | |
| TGFβ at 5 ng/ml | 11.604 | 372 | p < 0.01 | 14.746 | 568 | p < 0.01 |
| quinoa peptides 0.05% | 2.799 | 14 | p < 0.01 | 3.429 | 55 | p < 0.01 |

TABLE 12-continued

Dosage of MMP-9 protein in the supernatants of keratinocytes.

| | Treatment 48 h | | | Treatment 72 h | | |
|---|---|---|---|---|---|---|
| | Amount of MMP-9* | % A | Student t test | Amount of MMP-9* | % A | Student t test |
| quinoa peptides 0.1% | 2.988 | 22 | p < 0.01 | 3.472 | 57 | p < 0.01 |

*ng/mL/OD neutral red;
A = increase d. Evaluation of the Functional Effect of *Quinoa* Peptides on the Migration of Keratinocytes The functional effect of *quinoa* peptides on the migration of keratinocytes was evaluated in an artificial scar after blocking cell proliferation.

Visual comparison of the photographs illustrating the cells treated with *quinoa* peptides, with non-treated cells, provides the conclusion that *quinoa* peptides promote cell migration: presence of more keratinocytes in the artificial scar of the cells treated with *quinoa* peptides. This increase in the migration of keratinocytes was quantified by counting the number of migrating cells in the artificial wound. Thus, *quinoa* peptides increase migration of keratinocytes by +67%.

c. Effect of *Quinoa* Peptides on the Proliferation of Keratinocytes

In order to verify whether the *quinoa* peptides are associated with the process of proliferation of keratinocytes (=second step of the re-epithelialization mechanism), a cell viability MTT test was conducted, in order to evaluate the direct action of *quinoa* peptides on cell proliferation. As shown in Table 13, treatment with Trans Retinoic Acid (ATRA)=positive control, induces a proliferation rate of +36%. In the same way, the *quinoa* peptides tested at 0.05 and 0.1% DM very significantly stimulate proliferation of the keratinocytes, with an increase of the order of +20%.

TABLE 13 proliferation of keratinocytes

| | Mean OD570 (MTT) | Standard Deviation | % of proliferation | Student t test |
|---|---|---|---|---|
| Negative control | 1.003 | 0.050 | 100 | p < 0.01 |
| ATRA at 1 µM | 1.361 | 0.140 | 136 | p < 0.01 |
| quinoa peptides 0.05% | 1.156 | 0.075 | 115 | p < 0.01 |
| quinoa peptides 0.1% | 1.201 | 0.071 | 120 | p < 0.01 | f. Study of the Synthesis of KGF by Fibroblasts

During re-epithelization, the keratinocytes proliferation process is carried under the influence of many factors which may be secreted by the keratinocytes or by the fibroblasts of the dermis: production of KGF (Keratinocytes Growth Factor). In response to the KGF overexpressed by fibroblasts, keratinocytes multiply and thus cover more rapidly the lesion. The effect of *quinoa* peptides on the secretion of this factor by dermal fibroblasts, after a treatment of 24 and 48 hours, was evaluated. In the Table 14, it is confirmed that the synthesis of KGF increased in the presence of IL1α. On the other hand, *quinoa* peptides tested with 0.05 and 0.1% DM very significantly stimulate secretion of KGF by fibroblasts. This stimulation is dose-dependent and very substantial after 24 hours of treatment (multiplication by 5 and 7 as compared with the control without any treatment).

TABLE 14

Dosage of KGF in supernatants of fibroblasts.

| | Treatment 24 h | | | Treatment 48 h | | |
|---|---|---|---|---|---|---|
| | Amount of KGF* | % A | Student t test | Amount of KGF* | % A | Student t test |
| Control | 27.853 | | | 80.884 | | |
| TGFβ at 5 ng/ml | 147.886 | 431 | p < 0.01 | 352.387 | 336 | p < 0.01 |
| quinoa peptides 0.05% | 135.454 | 386 | p < 0.01 | 148.744 | 84 | p < 0.01 |
| quinoa peptides 0.1% | 194.650 | 599 | p < 0.01 | 160.405 | 98 | p < 0.01 |

*pg/mL/OD neutral red;
A = increase

Conclusion:

the whole of the studies presented here provided the demonstration of the role of *quinoa* peptides in epidermal healing. By stimulating both processes, *quinoa* peptides allow effective and fast restoration of the integrity of the skin.

The invention claimed is:

1. A method of treating a disorder related to dermal tissues, comprising administering an effective amount of a dermatological composition comprising a *quinoa Chenopodium quinoa* grain extract to a person in need thereof, wherein the *quinoa Chenopodium quinoa* grain extract is a peptide and oside extract, and wherein said disorder is acne, skin ageing, stretch marks, deep wounds, surface scars, cheilitises, the skin after stings, abrasions of the skin, skin spots or crusts, sensitive skin, hirsutism, or seborrhoeic dermatitis.

2. The method of claim 1, wherein the peptide and oside extract comprises 25 to 90% by weight of peptides and from 10 to 50% by weight of sugars, the percentages being expressed relative to the total weight of said peptide and oside extract.

3. The method of claim 1, wherein the *quinoa Chenopodium quinoa* grain extract is obtained by a method comprising the enzymatic hydrolysis of *quinoa Chenopodium quinoa* proteins.

4. The method of claim 3, wherein the peptide and oside extract is obtained by a method comprising the following successive steps:
   a) extracting a raw oil and a cake from *quinoa Chenopodium quinoa* grains and recovering said cake;
   b) washing said recovered cake with water or with a water/alcohol mixture to only retain a protein portion, and then
   c) solubilizing the protein portion;
   d) concentrating the solubilized protein portion and enzymatically hydrolyzing the concentrated protein portion into peptides; and
   e) purifying and recovering the peptide and oside extract.

5. The method of claim 4, further comprising removing fibers prior to concentrating the proteins in step d).

* * * * *